[19] United States Patent
Watanabe et al.

[11] 4,218,432
[45] Aug. 19, 1980

[54] COLORING AGENT AND A COMPOSITION INCLUDING THE SAME FOR COLORING TOILET BOWL FLUSHING WATER

[75] Inventors: Koichi Watanabe, Hirakata; Hiroaki Harada; Akira Kotone, both of Nara, all of Japan

[73] Assignee: Yamamoto Kagaku Gosei Co., Ltd., Osaka, Japan

[21] Appl. No.: 919,693

[22] Filed: Jun. 27, 1978

[30] Foreign Application Priority Data

Jun. 28, 1977 [JP] Japan .................................. 52/77463
Jun. 28, 1977 [JP] Japan .................................. 52/77464
May 22, 1978 [JP] Japan .................................. 53/61296

[51] Int. Cl.$^2$ ..................... A01N 17/00; C09B 69/00
[52] U.S. Cl. ................................ 424/14; 252/522 A; 252/106; 252/522 R; 252/542; 424/78; 542/444
[58] Field of Search .................... 424/14, 78; 542/444; 252/106, 175, 177, 522, 542; 8/76

[56] References Cited

U.S. PATENT DOCUMENTS

| 2,533,206 | 12/1950 | Dent et al. | 542/444 |
| 2,840,443 | 6/1958 | Smith | 542/444 |
| 3,785,769 | 1/1974 | Renfrew | 542/444 |
| 3,865,817 | 2/1975 | Kobayashi et al. | 542/444 |
| 3,970,576 | 7/1976 | Carmello et al. | 252/106 |

Primary Examiner—V. D. Turner
Attorney, Agent, or Firm—Wenderoth, Lind & Ponack

[57] ABSTRACT

A coloring agent which can be substantially completely decolored either through a treatment by a low concentration of chlorine type decoloring agents such as chlorine and hypochlorite or through a biological treatment usually employed in sewage treatments. The coloring agent is a certain group of polymethlyne compounds having at both the ends of the polymethyne chain pyrazolone structures. A composition comprising at least one of the coloring agents and additives in solution or solid form suitably used for coloring toilet bowl flushing water.

19 Claims, No Drawings

COLORING AGENT AND A COMPOSITION INCLUDING THE SAME FOR COLORING TOILET BOWL FLUSHING WATER

This invention relates to a coloring agent and a composition which can be completely decolored by simple treatments. More particularly, the invention relates to a coloring agent and a composition suitably used for coloring toilet bowl flushing water which in turn can be completely decolored by a very low concentration of chlorine type decoloring agents and even by usual biological treatments.

Conventionally, blue flushing water or disinfecting solution has been used for flushing a toilet bowl at home and offices so that the bowl is visually clean and hygienic. In particular, when a limited amount of water should be repeatedly used for flushing a toilet bowl as is the case with vehicles, aeroplanes and vessels, blue flushing water is most preferably used since it conceals an unpleasant color of human waste contained therein and keeps the flushing water visually clean after the repeated use.

However, many of the coloring agents which have been conventionally used for making flushing water blue are not at all decolored or decolored only with incompleteness by means of usual sewage treatments, resulting in secondary water pollution due to the colored waste water discharged.

In more detail, the conventional blue coloring agents such as Methylene Blue and threne type compounds which have been in a wide use, however, are not decolored under neutral or alkaline conditions as waste flushing water usually is, not only through usual sewage treatments such as an aeration and an activated sludge method, but also through an advanced treatment using an excess of chlorine or hypochlorite.

Therefore, there has been an increasing requirement for a coloring agent or a composition which can be completely decolored by simple treatments, particularly for a coloring agent or a composition suitably used for coloring toilet bowl flushing water which in turn can be completely decolored in simple manners usually employed when the colored flushing water is discharged.

The inventors, after an extensive study on a wide variety of coloring agents, have found that a certain group of polymethyne type coloring agents having at both the ends pyrazolone structures can be decolored substantially completely by chlorine or hypochlorite of a very low concentration and even by usual biological treatments such as an activated sludge method, thereby reaching the invention.

An object of the present invention is, therefore, to provide a coloring agent and a composition which can be substantially completely decolored by simple treatments, and in particular, to provide a coloring agent and a composition suitably used for coloring toilet bowl flushing water which can be substantially completely decolored by usual waste water treatments.

Other objects and features of the invention will be apparent from the following description with reference to preferred embodiments.

A coloring agent of the invention has the general formula:

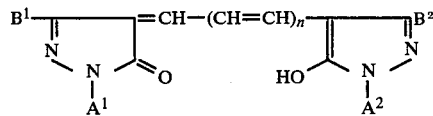

$A^1$ and $A^2$ are independently selected from the group consisting of hydrogen, lower alkyls of 1 to 4 carbons, most preferably methyl, phenyl, lower alkyls of 1 to 4 carbons having a water soluble radical selected from the group consisting of carboxylates and sulfonates formulated as —COOM and —SO$_3$M respectively, phenyls and naphthyls both having at least one of the water soluble radicals as defined above, wherein M is selected from the group consisting of alkali metals, alkaline earth metals, ammonium and lower alkyl ammoniums, preferably alkali metals such as potassium and sodium in view of easiness and cost in the production of the coloring agent. However, M may be an alkaline earth metal such as calcium, or lower alkyl ammoniums such as dimethylammonium, trimethylammonium and tetraethylammonium.

The water soluble radical is either directly connected to phenyl and naphthyl or indirectly connected to the aromatic ring through a lower alkylene radical of 1 to 4 carbons, typically methylene.

Furthermore, the water soluble radical may be connected to the aromatic ring through a radical containing heterocyclics. For example, $A^1$ and $A^2$ can be

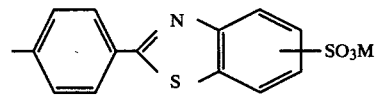

$B^1$ and $B^2$ are independently selected from the group consisting of lower alkyls of 1 to 4 carbons, most preferably methyl, carboxyl, lower alkoxycarbonyls wherein the alkoxy has 1 to 4 carbons, hydroxyl and lower alkoxys of 1 to 4 carbons, preferably methoxy and ethoxy. The carboxyl and the alkoxycarbonyl can be connected to the pyrazolone ring through lower alkylene radicals of 1 to 4 carbons, typically methylene.

$B^1$ and $B^2$ can also be independently selected from the group consisting of lower alkyls of 1 to 4 carbons, phenyls and naphthyls each having at least one of the water soluble radicals which are previously defined herein.

Other examples of $B^1$ and/or $B^2$ are non-substituted or N-substituted amino, carbamoyl, amido and ureido radicals in which the N-substituents are, for example, lower alkyls of 1 to 4 carbons, preferably methyl, and phenyl which may have the water soluble radical. Some typical examples of the above radicals are —NH$_2$, —NHCH$_3$, —N(CH$_3$)$_2$, —NH—C$_6$H$_5$, —CONH$_2$, —CONHCH$_3$, —CONH—C$_6$H$_5$, —CONH—C$_6$H$_4$—COOH, —NHCOCH$_3$, —NHCO—C$_6$H$_5$, —NHCO—C$_6$H$_4$—SO$_3$M, —NHCONHCH$_3$, —NHCONH—C$_6$H$_5$, —NHCOCH$_2$CH$_2$SO$_3$M and the like.

The numeral n in the above general formula of the coloring agent is 0, 1 or 2. The coloring agents with n of 0 or 1 show yellow to red when dissolved into water, and the coloring agents with n of 2 generally show blue when dissolved into water. According to the invention, these blue coloring agents are preferable since they conceal an unpleasant color of human waste contained therein most effectively as well as they keep the flushing water visually clean and fresh after the repeated use through the color of blue. However, if necessary, the coloring agent with n of 0 or 1 can be used alone or together with the coloring agent with n of 2.
Some typical and preferable examples of the coloring agents of the invention are listed below.
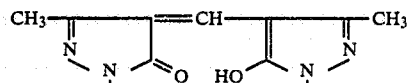
1
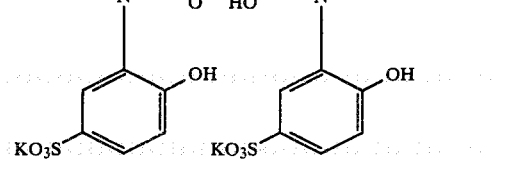
2
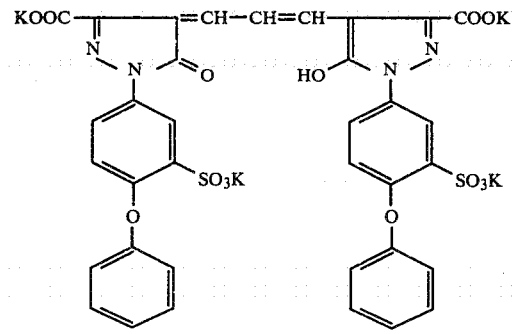
3
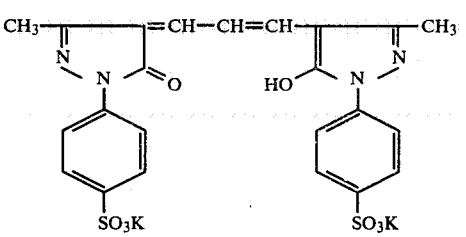
4
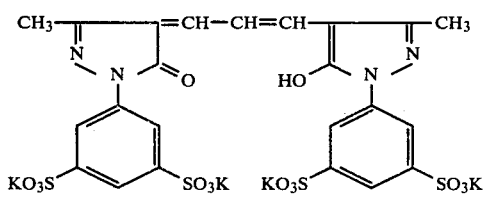
5
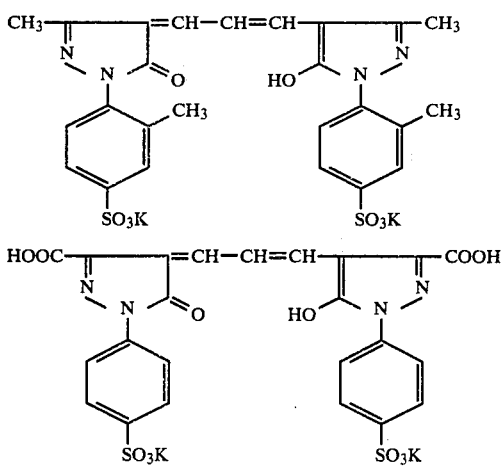
6

-continued
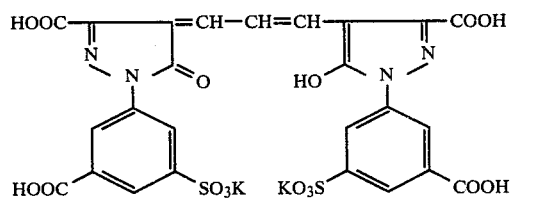
7
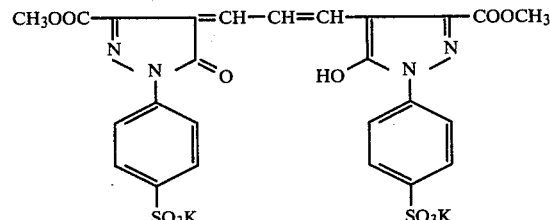
8
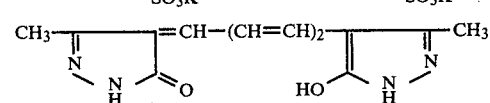
9
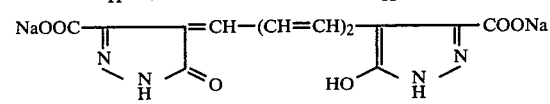
10
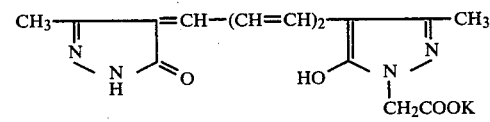
11
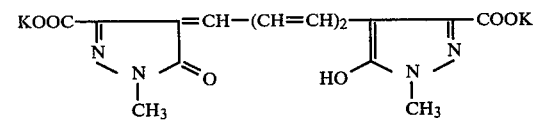
12
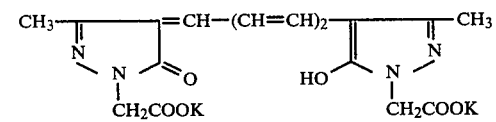
13
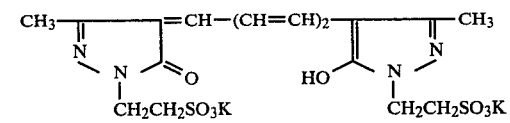
14
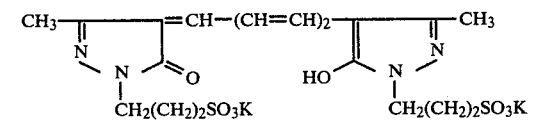
15
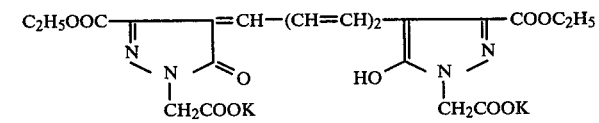
16
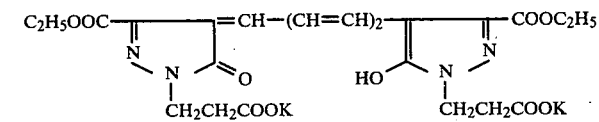
17
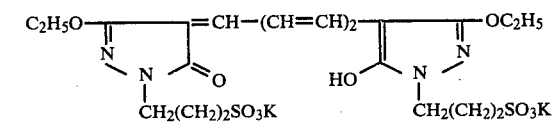
18
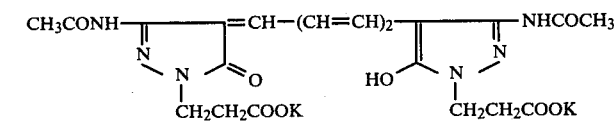
19

-continued
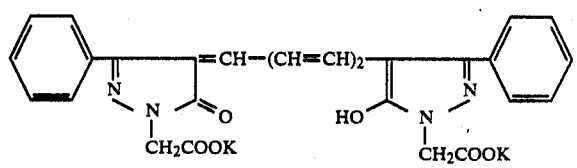 20
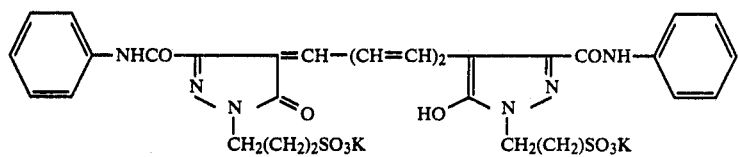 21
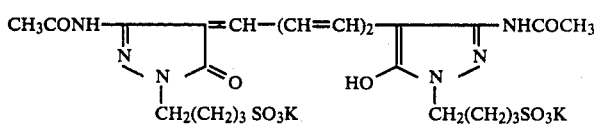 22
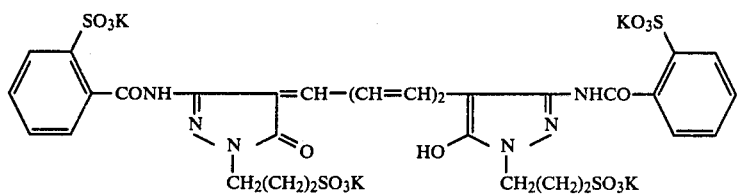 23
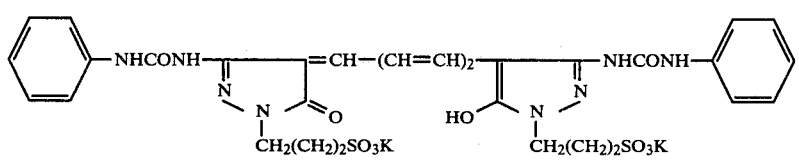 24
 25
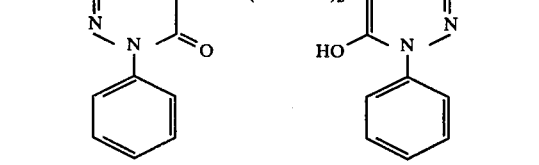 26
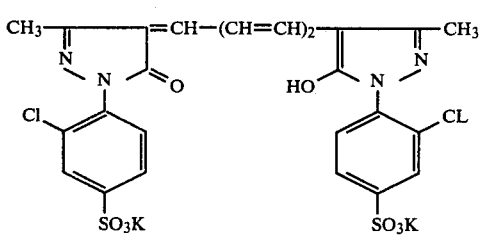 27
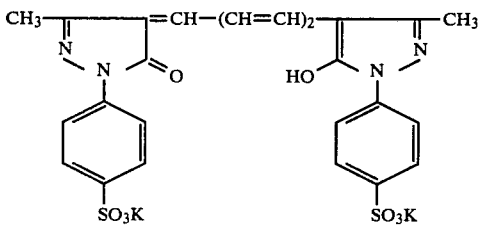 28

-continued
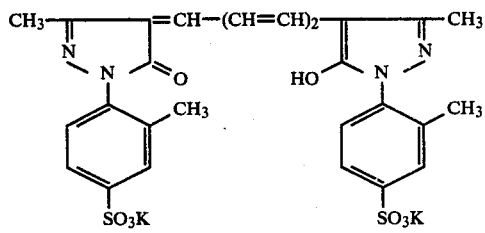 29
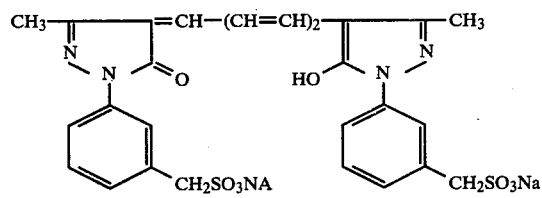 30
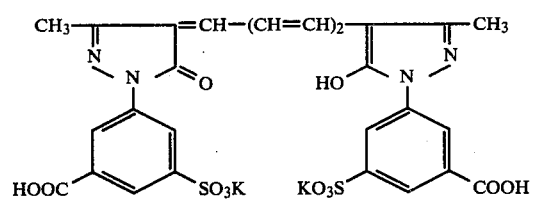 31
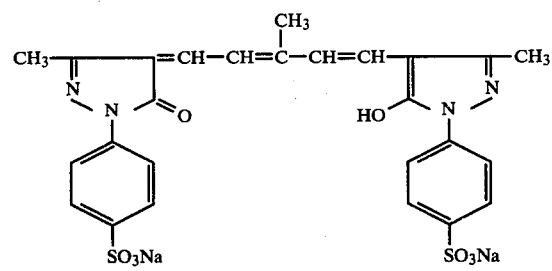 32
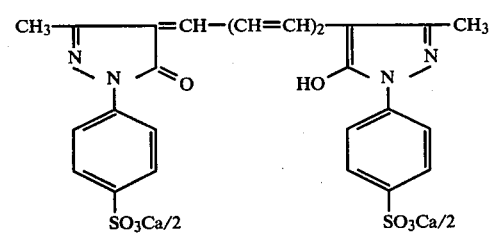 33
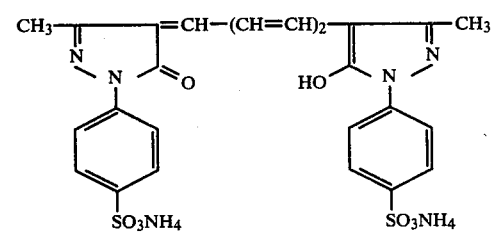 34
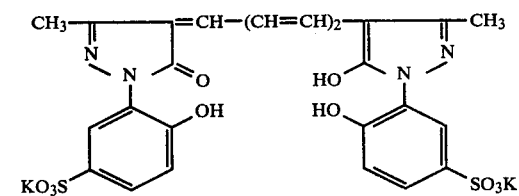 35

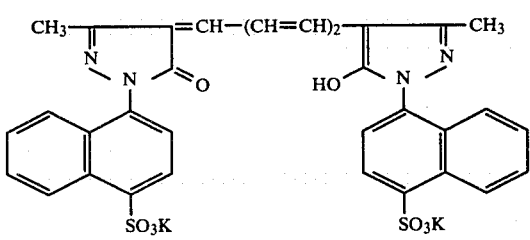
36
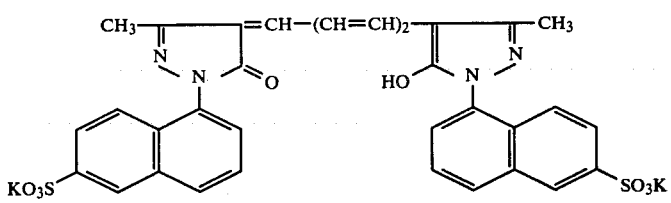
37
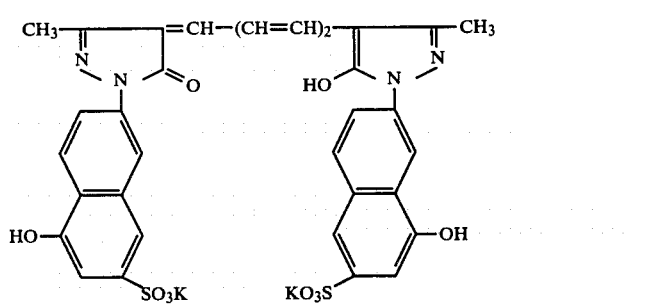
38
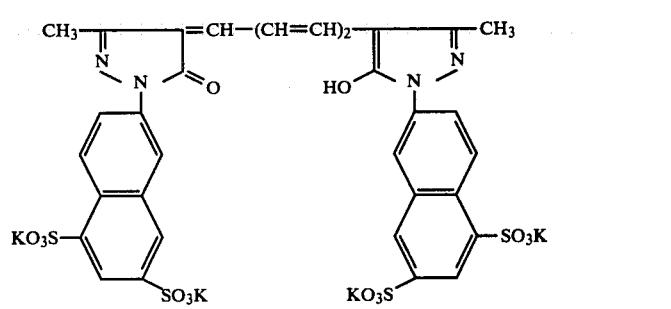
39
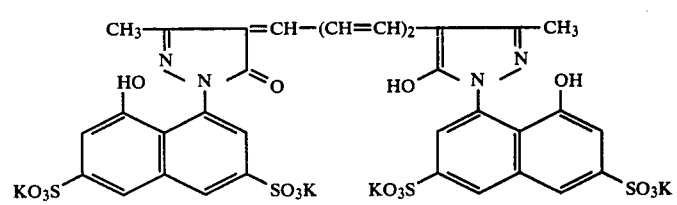
40
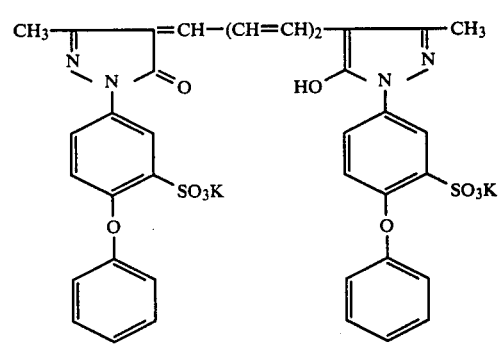
41

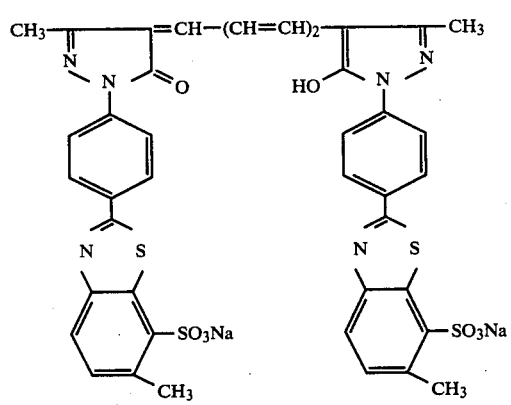
42
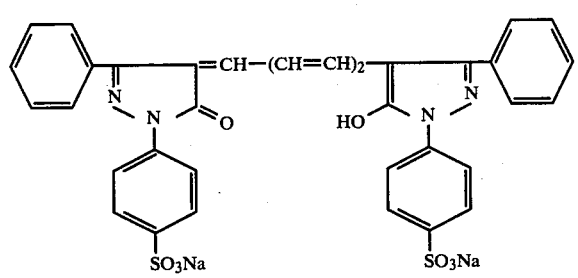
43
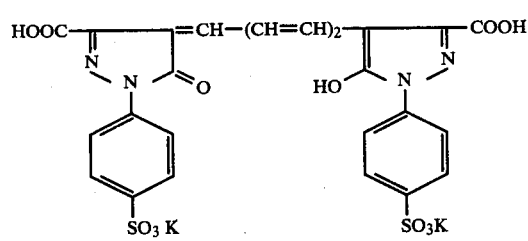
44
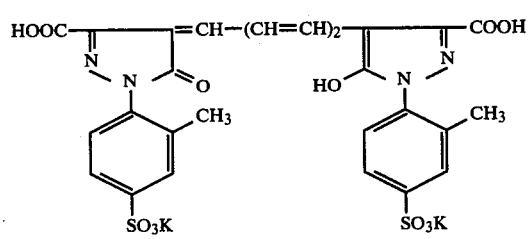
45
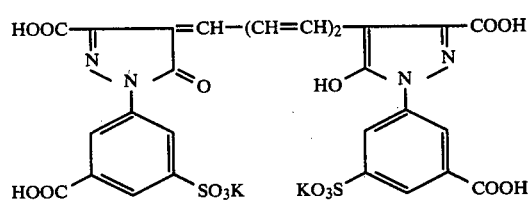
46
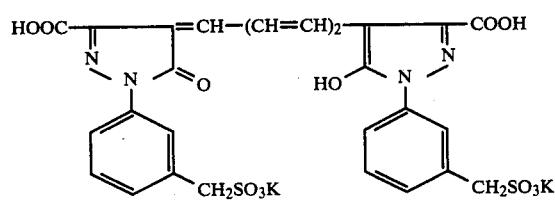
47

-continued
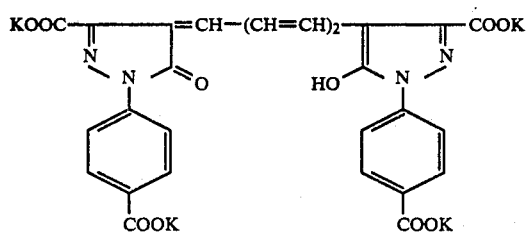 48
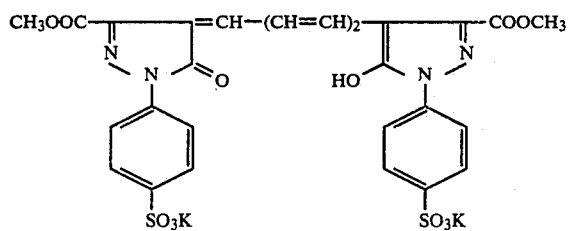 49
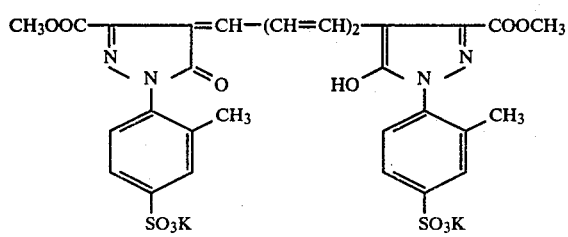 50
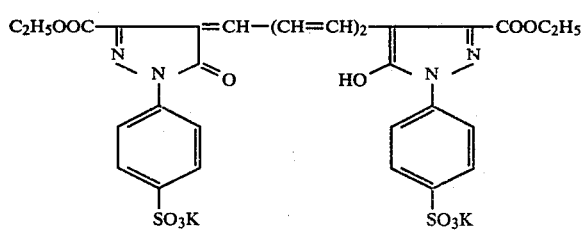 51
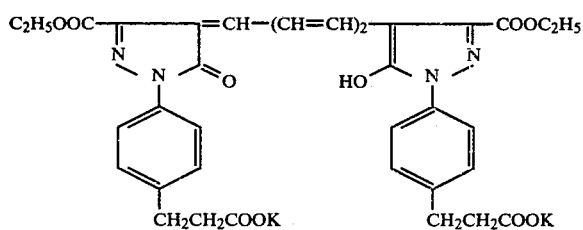 52
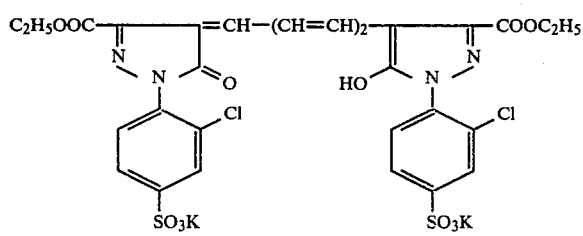 53
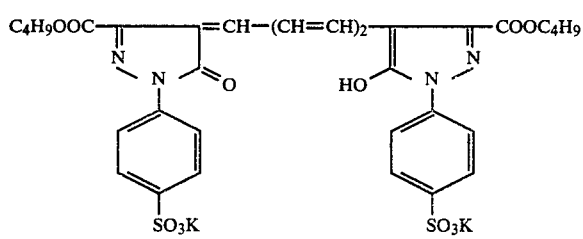 54

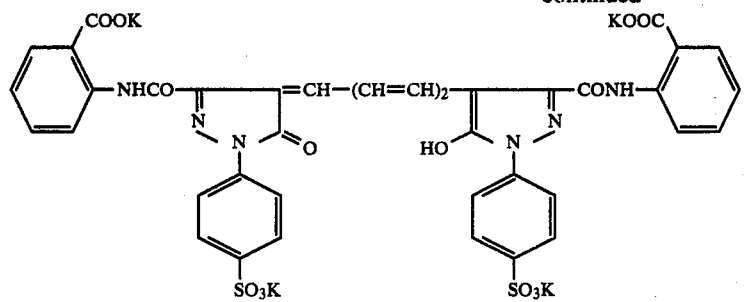
55
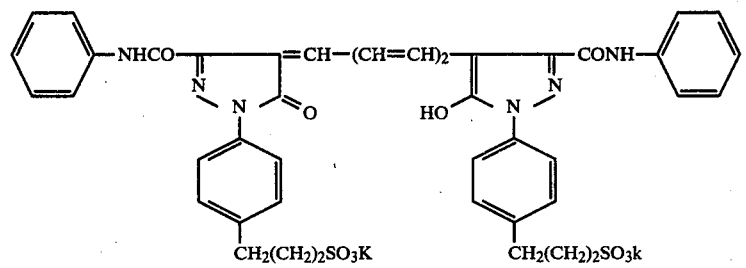
56
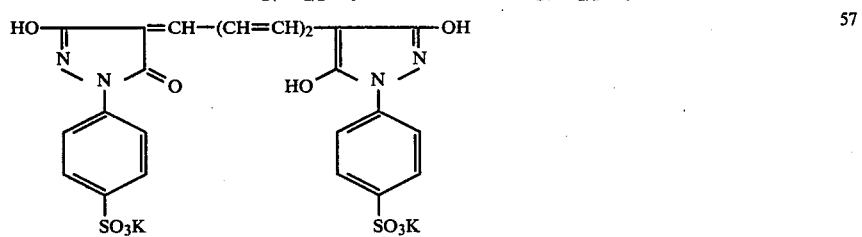
57
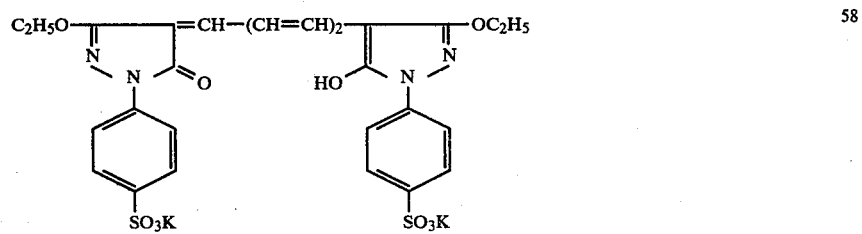
58
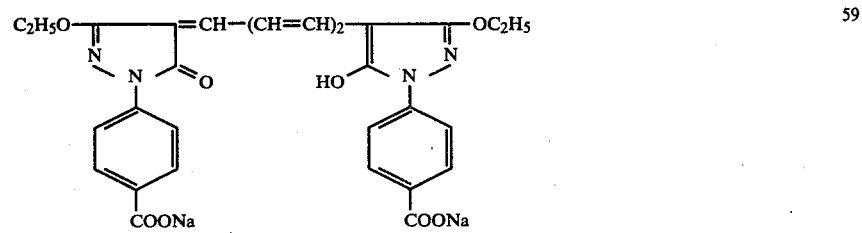
59
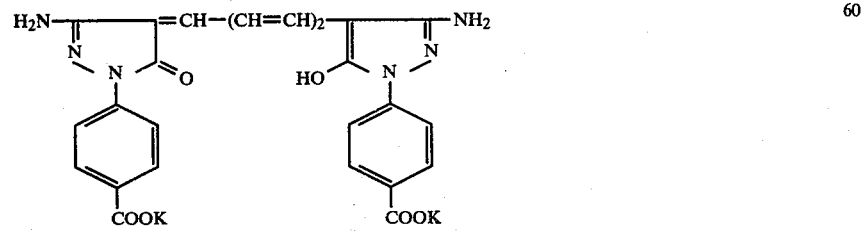
60
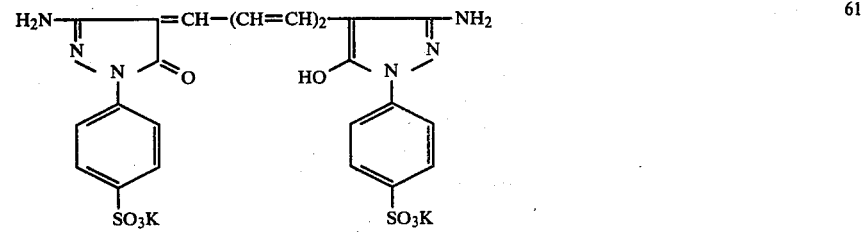
61

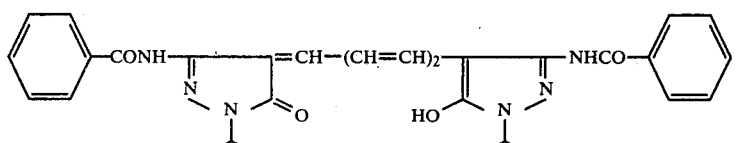

62

63

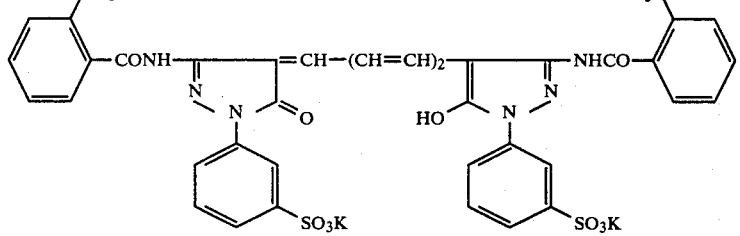

64

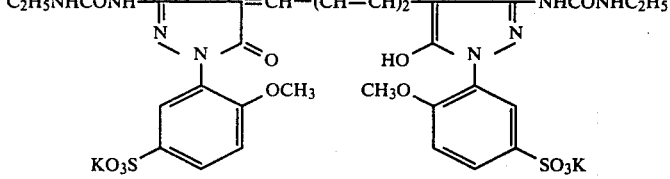

65

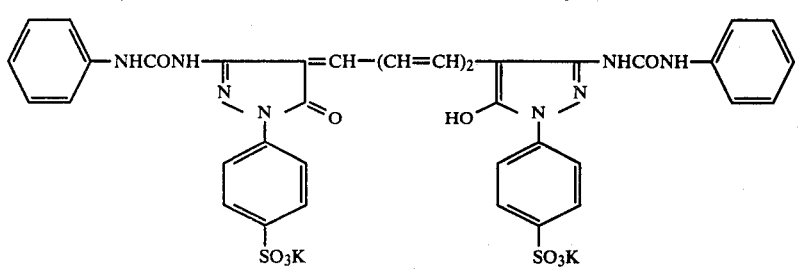

66

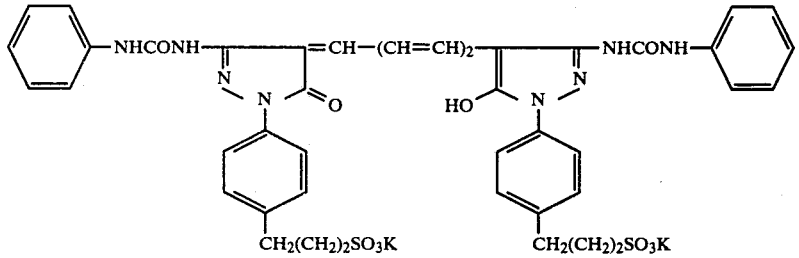

As above listed, the coloring agents of the invention usually have the same pyrazolone structure at both the ends of the polymethyne chain, and it is preferable that at least one of the two pairs, one $A^1$ and $A^2$, and the other $B^1$ and $B^2$, have the water soluble radical. However, when $A^1$ and $A^2$ are hydrogens, $B^1$ and $B^2$ can be methyls as shown as the coloring agent 9 since the coloring agent has a sufficient solubility in water. When $A^1$ and $A^2$ are hydrocarbon radicals such as methyls and phenyls, $B^1$ and $B^2$ are preferably —COOM so that the compound has a sufficient solubility in water, as shown as the coloring agents 12 and 25.

When $A^1$ and $A^2$ are lower alkyls having the water soluble radical, they are preferably formulated as —(CH$_2$)$_p$COOM or —(CH$_2$)$_q$SO$_3$M wherein p is 1 or 2 and q is 1, 2, 3 or 4.

In general, when $A^1$ and $A^2$ have at least one of the water soluble radical, that is, $A^1$ and $A^2$ are lower alkyls as formulated above, phenyls and naphthyls having the water soluble radical, $B^1$ and $B^2$ can be a wide variety of radicals, among which are lower alkyls of 1 to 4 carbons, typically methyl, phenyl, carboxyl, lower alkoxycarbonyls wherein the alkoxy has 1 to 4 carbons, hydroxyl, lower alkoxys of 1 to 4 carbons, phenoxy, etc. Furthermore, $B^1$ and $B^2$ can be non-substituted or N-substituted amino, carbamoyl, amido and ureido radicals as previously mentioned.

Phenyls and naphthyls as $A^1$, $A^2$, $B^1$ or $B^2$ can have other substituents such as lower alkyls, typically methyl, lower alkoxys, typically methoxy, phenoxy, hydroxyl and halogens such as chlorine and bromine, together with or without the water soluble radical.

It is to be noted that in the coloring agents of the invention, $A^1$ and $B^1$ may be different from $A^2$ and $B^2$, respectively, as shown as the coloring agent 11, and that a hydrogen may be replaced with a lower alkyl, typically methyl, as shown as the coloring agent 32.

According to the invention, one or more of the coloring agents are mixed with disinfectants, surfactants, chelating agents, perfumes and the like to form into an aquaous composition, which is, for example, added to flushing water manually or automatically when a toilet bowl is flushed. More preferably, however, one or more of the coloring agents are mixed with binders, in addition to the above mentioned additives if desired, to form a powdered or molded composition such as a pellet and a ball and are adapted to gradually dissolve in water. The molded composition is, for example, put into a reservoir containing flushing water so as to gradually dissolve therein, thereby providing colored flushing water.

In use of the coloring agent or the composition of the invention, it is dissolved in water so that the coloring agent is contained therein at a concentration of 0.0005 to 0.01 weight %, preferably 0.001 to 0.005 weight %. However, the concentration can be varied outside the above range, if desired.

Since the coloring agents of the invention can be substantially completely decolored through the treatment using a very small amount of chlorine or hypochlorite, the flushing water colored by the coloring agent or the composition causes no secondary water pollution due to the waste colored flushing water after usual sewage treatments.

An important feature of the coloring agents of the invention is that it can be substantially completely decolored even by biological treatments which are usually employed in sewage treatments. This biological decoloration is not apparent decoloration due to, for example, adsorption or coagulation of the coloring agent to bacteria, but chemical decoloration due to decomposition of the coloring agent by bacteria. Various biological treatments can be employed for decoloring the coloring agent of the invention such as aerobic methods among which are an activated sludge method and a trickling filtration method, and anaerobic treatments such as digestion. The examples of aerobes are Zoogloea and Sphaerotilus, and those of anaerobes are methane bacteria and Pseudomonas.

Disinfectants which can be mixed with the coloring agent are, for example, quaternary ammonium salts such as trimethylbenzylammonium chloride, trimethyldodecylammonium chloride, dodecyldimethylbenzylammonium chloride, dodecylpyridinium chlorode, dichlorobenzylmethyldodecylammonium chloride, Aerosol M, i.e.,

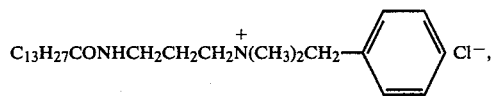

Zephirol M, i.e.,

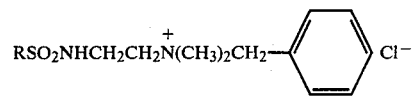

wherein R represents a higher alkyl radical), Emcol E-607, i.e.,

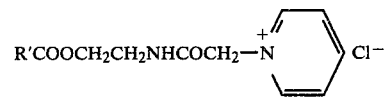

wherein R' represents a higher alkyl radical), and octylphenoxyethoxyethyldimethylbenzylammonium chloride; organic sulfur type disinfectants such as tetramethylthiuram, sodium methylthiocarbamate, ammonium methylthiocarbamate, N-(p-phenol)dimethylthiocarbamate, 1,2-benzoisothiazolone and methylenebisthiocyanate; organic nitrogen type disinfectants such as sodium azide, N-(p-phenol)trichloroalkylcyanide, nitrofurane, halogenated acetoamide, 1,3-dinonylbenzimidazolium bromide, 1-(2-hydroxyethyl)-1-benzyl-2-tridecylimidazolium bromide, tris(hydroxymethyl)nitromethane, 1-N-piperazino-2-nitropropylbenzene, and 2,6-bis(dimethylaminomethyl)cyclohexanone; amphoteric disinfectants such as dodecyl(diaminoethyl)glycine, $\beta$-alkylaminopropionate, dodecyldimethylbetaine and cetyldimethylbetaine; chlorine type disinfectants such as pentachlorophenol, trichlorophenol, o-benzyl-p-chlorophenol and 2,2'-thiobis(4,6-dichlorophenol); and organotin disinfectants such as tributyltin oxide.

One of these disinfectants is mixed with the coloring agent or incorporated into the composition, if desired together with other disinfectants. Since some disinfectants are more disinfective under acidic conditions and some under alkaline conditions, disinfectants and the amount thereof to be added to the coloring agent are suitably chosen in accordance with the purpose of coloring. If necessary, in order to increase the disinfective power of disinfectants, pH adjusting agents are used together with the disinfectants, such as soda ash, tetrasodium pyrophophate, sodium tripolyphosphate, acetic acid, sodium acetate, citric acid, sodium citrate, tartaric acid, sodium tartrate, sodium silicate, calcium hydroxide and sodium hydrogencarbonate.

Perfumes or deodorants can be mixed with the coloring agent or incorporated into the composition. They are, for example, anisaldehyde, ethyl acetoacetate, anisole, anethole, amylcinnamic aldehyde, methyl anthranilate, methyl benzoate, geranyl formate, cinnamic alcohol, cinnamic aldehyde, terpinyl acetate, butylcyclohexyl acetate, benzyl acetate, citronellol, methyl salicylate, terpineol, $\beta$-phenylethyl alcohol, benzyl alcohol, methylacetophenone and menthol. Compounded perfumes of these can be also used.

Surfactants which can be used together with the coloring agent are, for example, sodium and potassium salts of various fatty acids, sodium alkylbenzenesulfonates, sulfuric acid esters of higher alcohols, $\alpha$-olefine sulfonates, polyoxyethylenealkylether sulfates, polyoxyethylenealkylether, polyoxyethylenealkylphenylether, fatty acid esters of polyoxyethyleneglycols, fatty acid esters of propyleneglycol and the like.

If desired, chelating agents are added to the coloring agents, such as sodium tripolyphosphate, sodium hexametaphosphate, ethylenediaminetetraacetic acid, nitrilotriacetic acid, aminomethylenephosphates, methylenephosphoric acid and phosphonocarboxylates.

Binders mixed with the coloring agent and other additives as above mentioned to form the solid composition of the invention are, for example, carboxymethylcellulose, carboxymethyl starch, polyethylene glycol, polypropylene glycol and polyvinyl alcohol. A mixture of these binders can be also used. In forming the solid composition with the binders, fillers or extenders can be used if desired in addition to the above additives. Sodium sulfate, potassium sulfate, ammonium sulfate and urea are examples of the filler or extender.

In forming the solid composition of the invention, polyethylene glycol as an example of binder, having preferably a polymerization degree of about 6000-20000, is melted, mixed thoroughly with at least one of the coloring agents and if necessary also with disinfectants, surfactants, perfumes, chelating agents, and fillers, and cooled into a molded composition of desired shape and size. When a liquid perfume is used, a water soluble solid is in advance formed which comprises the perfume, polyethylene glycol and alkylphenol polyethyleneoxides, and the water soluble solid is melted and mixed with the coloring agents. An eutectic solid is a typical example of such a water soluble solid.

The coloring agents of the invention can be produced easily by known conventional methods. For example, the coloring agents with n of 0, 1 and 2 are obtained by condensation of 2 moles of pyrazolone derivatives with 1 mole either of ethyl orthoformate or of diphenylformamidine, 1 mole either of propene dianil hydrochloride or of tetramethoxypropane, and 1 mole either of glutacondialdehyde dianil hydrochloride, dinitrophenylpyridinium chloride or of N-cyanopyridinium brobide, respectively, in the presence of a basic catalyst such as triethylamine, pyridine, piperidine and ammonia in a solvent in which the pyrazolone derivative is soluble. As solvents are used, for example, methanol, ethanol, ethyleneglycol monomethylether, dimethylformamide and dimethylsulfoxide.

The condensation reaction is usually carried out at a temperature below the boiling point of the solvent under a normal pressure, preferably at a lower temperature, for example, at 40°-70° C. since some coloring agents are unstable at a higher temperature.

As is apparent, a mixture of each 1 mole of pyrazolone derivative different in the structure from each other is reacted, for example, with glutacondialdehyde dianil hydrochloride to form a mixture of three different coloring agents. This mixture can be used as it is. If necessary, the mixture may be separated into each induvidual coloring agent.

Preferred embodiments of the invention will now be described below.

PART A—SYNTHESES OF COLORING AGENTS

Example 1

In 30 weight parts of anhydrous ethanol were dissolved 5.5 weight parts of 1-(2'-hydroxy-5'-sulfophenyl)-3-methyl-5-pyrazolone and 2.5 weight parts of diphenylformamidine together with 5 weight parts of triethylamine. The mixture was stirred for 1 hour at 50° C., and 28.5 weight parts of anhydrous ethanol solution containing 3.5 weight parts of anhydrous potassium acetate was added thereto to precipitate the product, which was filtered off, washed with acetone and dried to give 5 weight parts of the coloring agent 1, which shows yellow when dissolved in water.

Example 2

In 70 weight parts of anhydrous ethanol were dissolved 7.5 weight parts of 1-(p-phenoxy-m-sulfo)phenyl-3-carboxy-5-pyrazolone and 2.6 weight parts of propene dianil hydrochloride together with 6 weight parts of triethylamine, and the mixture was stirred at 40°-50° C. for 2 hours. The product precipitated on the addition of 13.6 weight parts of an aqueous solution containing 3.6 weight parts of anhydrous potassium carbonate to the reaction mixture. The product was filtered off, washed with acetone and dried to give 8.5 weight parts of a red crystalline powder of the coloring agent 2, which shows red in water.

Example 3

In 40 weight parts of anhydrous methanol were dissolved 5 weight parts of 1-(4'-sulfophenyl)-3-methyl-5-pyrazolone, 2.6 weight parts of propene dianil hydrochloride and 3.5 weight parts of triethylamine. The mixture was refluxed for 3 hours on a hot water bath with stirring. To the reaction mixture was added 33.1 weight parts of an anhydrous methanol solution containing 3.1 weight parts of anhydrous potassium acetate to precipitate the product. The product was separated from the solution by filtration, washed with acetone and dried to give the coloring agent 3 as a red powder. This shows red in water.

Example 4

In 50 weight parts of anhydrous ethanol were dissolved 6.2 weight parts of glutacondialdehyde dianil hydrochloride, 11 weight parts of triethylamine and 4.3 weight parts of 3-methyl-5-pyrazolone, and the mixture was heated at 40°-50° C. for 2 hours with stirring. The reaction mixture was then cooled to precipitate the product, which was filtered off, washed with acetone and dried to give 5.5 weight parts of black to dark blue crystalline powder of the coloring agent 9, which shows blue when dissolved in water.

Example 5

In 60 weight parts of anhydrous ethanol were dissolved 2 weight parts (0.02 moles) of 3-methyl-5-pyrazolone, 3.2 weight parts (0.02 moles) of 1-carboxymethyl-3-methyl-5-pyrazolone, 5.7 weight parts (0.02 moles) of glutacondialdehyde dianil hydrochloride and 7 weight parts of triethylamine. The mixture was stirred at 40° C. for 3 hours, and after the addition of 20 weight parts of a 30 weight % aqueous solution of anhydrous potassium carbonate, was further stirred overnight. The precipitated product was filtered off, washed with ethanol, and then with acetone, and dried to give 6 weight parts of a blue crystalline powder, which was a mixture of the three coloring agents, 9, 11 and 13. The mixed coloring agents dissolved in water to show blue.

Example 6

In 60 weight parts of anhydrous ethanol were dissolved 9.5 weight parts of 1-carboxymethyl-3-ethoxycarbonyl-5-pyrazolone and 6.2 weight parts of glutacondialdehyde dianil hydrochloride together with 11 weight parts of triethylamine, and the mixture was stirred at 40°-50° C. for 3 hours, then to which was added 5 weight parts of potassium carbonate. The precipitates were filtered off, washed with acetone and dried to give 13 weight parts of a dark blue crystalline powder of the coloring agent 16. The product dissolved in water to show blue.

Example 7

In 60 weight parts of anhydrous ethanol were dissolved 11 weight parts of 1-sulfopropyl-3-ethoxy-5-pyrazolone and 6.2 weight parts of glutacondialdehyde dianil hydrochloride. The mixture was reacted at 30°–40° C. for 3 hours while ammonia was bubbled thereinto. The reaction mixture, after the addition of 57 weight parts of anhydrous ethanol solution containing 7 weight parts of anhydrous potassium acetate thereto, was further stirred for 5 hours at an ambient temperature. The precipitated product was separated by filtration, washed with acetone and dried to give 14.8 weight parts of a dark blue crystalline powder of the coloring agent 18. The product dissolved in water to show blue.

Example 8

In 40 weight parts of anhydrous ethanol were dissolved 5.4 weight parts of 1-(3'-sulfomethylphenyl)-3-methyl-5-pyrazolone and 2.8 weight parts of 2,4-dinitrophenylpyridinium chloride. Into this solution was bubbled 0.6 weight parts of anhydrous ammonia for 1 hour with stirring, which was accompanied by a simultaneous increase in the temperature of the mixture up to about 40° C. After further one hour stirring at about 40° C., 33.1 weight parts of an anhydrous ethanol solution containing 3.1 weight parts of anhydrous sodium acetate was added to the reaction mixture. The precipitated product was filtered off, washed with anhydrous ethanol and then with acetone, and dried to give 6.2 weight parts of coloring agent 30. The product dissolved in water and gave blue water.

Example 9

In 70 weight parts of anhydrous ethanol were dissolved 14.2 weight parts of 1-[5'-hydroxy-7'-sulfonaphthalene-(2)]-3-methyl-5-pyrazolone and 6.2 weight parts of glutacondialdehyde dianil hydrochloride together with 11 weight parts of triethylamine, and reacted at 30°–40° C. for 3 hours with stirring. The reaction mixture was then treated in the same manner as in EXAMPLE 7. Seventeen weight parts of a dark blue crystalline powder of the coloring agent 38 were obtained, which shows blue when dissolved in water.

Example 10

In 40 weight parts of anhydrous ethanol were dissolved 6 weight parts of 1-(2'-methyl-4'-sulfophenyl)-2-carboxy-5-pyrazolone and 2.8 weight parts of 2,4-dinitrophenylpyridinium chloride. Anhydrous ammonia was bubbled into the mixture in the same manner as in EXAMPLE 8 to give 6.2 weight parts of the coloring agent 45, which dissolved in water and showed blue.

Example 11

In 60 weight parts of anhydrous ethanol were dissolved 12.6 weight parts of 1-(4'-sulfophenyl)-3-phenyl-5-pyrazolone and 6.2 weight parts of glutacondialdehyde dianil hydrochloride. The mixture was reacted at 30°–40° C. for 3 hours while anhydrous ammonia was bubbled thereinto. Upon adding 9 weight parts of an aquaous solution containing 4 weight parts of anhydrous sodium acetate, the product deposited as precipitates. The product was filtered off, washed and dried to give 16 weight parts of a dark blue crystalline powder of the coloring agent 43. The product dissolved in water to show blue.

Example 12

In 40 weight parts of anhydrous ethanol were dissolved 6 weight parts of 1-(4'-sulfophenyl)-3-carbomethoxy-5-pyrazolone and 2.9 weight parts of pentadiene dianil hydrochloride together with 3.5 weight parts of triethylamine. The mixture was reacted at 50° C. for 1 hour with stirring, followed by the same treatment as in EXAMPLE 8 to give 6.6 weight parts of the coloring agent 49. The product shows blue when dissolved in water.

PART B—PRODUCTION OF SOLID COMPOSITIONS

Example 13

Five weight parts of water was added to 88 weight parts of polyethylene glycol of polymerization degree of 6000 and was melted by heating. The liquid mixture was then thoroughly mixed with 1 weight part of the coloring agent 9 and 5 weight parts of a perfume. The mixture was poured into a cylindrical glass bottle and was then cooled to provide a solid composition. When immersed in a 20 l-capacity flushing water reservoir, the composition gradually dissolved therein to produce blue flushing water.

In the same manner as above except the use of the following coloring agents instead of the coling agent 9 in listed amounts in TABLE 1, respectively, solid compositions similar to the above were obtained.

TABLE 1

| Number of Coloring Agents | Amounts Used in Weight Parts |
|---|---|
| 17 | 2.3 |
| 24 | 3.3 |
| 26 | 2.8 |
| 28 | 2.8 |
| 29 | 2.0 |
| 30 | 2.0 |
| 31 | 2.2 |
| 32 | 2.2 |
| 36 | 3.0 |
| 43 | 3.0 |
| 47 | 2.2 |
| 63 | 4.0 |

Example 14

Using 60 weight parts of polyethylene glycol of a polymerization degree of 6000, 7 weight parts of water, 2.8 weight parts of the coloring agent 44 mixed with 0.2 weight parts of the coloring agent 3, 20 weight parts of urea, 5 parts of benzyltrimethylammonium chloride and 5 weight parts of a perfume, a solid composition was produced in the same manner as in EXAMPLE 13.

In the same manner as above using 2.7 weight parts of the coloring agent 45 mixed with 0.27 weight parts of the coloring agent 4, 2 weight parts of the coloring agent 13, and 2.5 weight parts of the coloring agent 16, respectively, solid compositions were obtained.

All of these molded compositions dissolved in water to provide blue and disinfective flushing water.

Example 15

Ten weight parts of polyethylene glycol of a polymerization degree of 10,000 was melted and thoroughly mixed with 12 weight parts of benzyltrimethylammonium chloride, 50 weight parts of urea, 5 weight parts of anhydrous sodium acetate, 3 weight parts of a perfume and 0.1 weight parts of the coloring agent 4 mixed with 1.3 weight parts of the coloring agent 49. The liquid mixture was solidified by cooling and then was powdered. The composition was gradually dissolve in 30 l of water to produce blue and disinfective flushing water.

Using 1.4 weight parts of the coloring agent 35, a powdered composition was obtained similar to the above.

Example 16

Twenty weight parts of benzyltrimethylammonium chloride, 50 weight parts of ethylenediaminetetraacetic acid, 100 weight parts of sodium sulfate, 5 weight parts of a perfume, 5 weight parts of a nonionic surfactant and 5 weight parts of the coloring agent 30 were thoroughly mixed to form a powdered composition. For example, the composition was wrapped in a polyvinylalcohol film and was immersed in a flushing water reservoir.

In the same manner as above except the use of the following coloring agents in the amounts listed in TABLE 2, respectively, instead of the coloring agent 30, powdered compositions similar to the above were obtained.

TABLE 2

| Number of Coloring Agents | Amounts Used in Weight Parts |
| --- | --- |
| 25 | 5.0 |
| 31 | 5.5 |
| 32 | 5.0 |
| 38 | 5.8 |
| 46 | 5.8 |
| 51 | 5.6 |
| 58 | 5.5 |

PART C—DECOLORATION OF COLORING AGENTS

Example 17

A powdered coloring composition was prepared by mixing thoroughly a colored agent with the following additives in amounts as listed in TABLE 3.

TABLE 3

| Compositions | Amounts Used (g) |
| --- | --- |
| Benzyltrimethylammonium Chloride | 18.6 |
| Urea | 35.7 |
| Anhydrous Sodium Acetate | 12.0 |
| Perfume | 5.0 |
| Polyethylene Glycol* | 7.0 |
| Coloring Agent | 1.0 |

*polymerization degree of 10000

The composition was dissolved in 10 l of water, and 100 cc portion of the colored water was, after the addition of 100 cc of human urine, allowed to stand for 24 hours for subjecting the mixture to decoloration test by an aquaous solution of 0.05 weight % hypochlorite sodium. The results on some coloring agents are shown in TABLE 4.

As apparent, the coloring agent of the invention was decolored by the addition of only 3.2 cc of the hypochlorite solution, which was corresponding to about 8 ppm, but the conventional coloring agents were not decolored even by the addition of several hundred cubic centimeters.

TABLE 4

| Coloring Agent | Amounts of Hypo-Chlorite (cc) | Observations |
| --- | --- | --- |
| 27 | 3.2 | decolored |
| Methylene Blue (C.I.52015) | 250 | not decolored |
| Acid Brilliant Blue AF (C.I.42080) | 250 | not decolored |
| Kayarus Supra Blue FFR6 (C.I.51320) | 250 | not decolored |
| Nichilon Pure Blue 7G | 300 | not decolored |

Example 18

In the same as in EXAMPLE 17, powdered compositions were prepared from coloring agents and additives as listed in TABLE 5, and subjected to the decoloration test. The results were shown in TABLE 6.

TABLE 5

| Compositions | Amounts Used (g) |
| --- | --- |
| Benzyltrimethylammonium Chloride | 20.0 |
| Urea | 37.0 |
| Anhydrous Sodium Acetate | 12.0 |
| Perfume | 5.0 |
| Polyethylene Glycol* | 7.0 |
| Coloring Agent | 0.9 |

*polymerization degree of 10000

TABLE 6

| Coloring Agents | Amounts of Hypo-Chlorite (cc) | Observations |
| --- | --- | --- |
| 20 | 4.2 | decolored |
| 25 | 3.2 | decolored |
| 36 | 4.3 | decolored |
| Methylene Blue (C.I.52015) | 250 | not decolored |
| Acid Brilliant Blue AF (C.I.42080) | 250 | not decolored |
| Kayarus Supra Blue FFR6 (C.I.51320) | 250 | not decolored |
| Nichilon Pure Blue 7G | 300 | not decolored |

Example 19

Decoloration tests were carried out using activated sludges. A powdered composition prepared using the coloring agent 27 in the same manner as in EXAMPLE 17 was dissolved in water so as to be contained therein in concentrations of 0.25, 0.15, 0.075, 0.025 and 0.0125 weight %, respectively. Each 400 cc portion of the water thus colored was put into an 1 l-capacity beaker, to each of which was added 200 cc of activated sludges with MLSS of 8200 g/cc and COD of 2200 g/cc from Sakai Sewage Treatment Plant, Osaka, Japan together with glucose and glutamic acid as standards so that the calculated BOD thereof is 6100 g/cc.

After aeration for a predetermined period as listed in TABLE 7, a portion of the mixture sample in each beaker was centrifuged and filtered. The absorptivity of each filtrate thus obtained was determined at 610 mμ, the maximum absorption wavelength of the coloring agent 27, using water as a control.

As shown in TABLE 7, the colored water containing 0.025 weight % of the composition was decolored by the activated sludges only in one day, and even the water containing 0.25 weight % of the composition in 7 days.

TABLE 7

| Concentrations of Compositions (Weight %) | Absorptivity (%) After Aeration For | | | |
|---|---|---|---|---|
| | 0 | 1 | 2 | 7 |
| | | Days | | |
| 0.25 | 100 | 68.5 | 29.6 | 0 |
| 0.15 | 100 | 60.6 | 27.2 | 0 |
| 0.075 | 100 | 46.8 | 12.5 | 0 |
| 0.025 | 100 | 0 | 0 | 0 |
| 0.0125 | 100 | 0 | 0 | 0 |

The same experiments on a composition containing Nichilon Pure Blue 7G as a coloring agent, however, revealed that the colored water containing the composition in 0.0125 weight % was not decolored, but resulted only in coloration of the activated sludges.

Example 20

In the same manner as in EXAMPLE 18, a powdered composition containing the coloring agent 36 was prepared and in the same manner as in EXAMPLE 19 the composition was subjected to the decoloration test using activated sludges with MLSS of 8600 g/cc and COD of 2900 g/cc from the Sakai Plant. The results were shown in TABLE 8, in which the absorptivity was determined at 613 m$\mu$, the maximum absorption wave length of the coloring agent 36, with water as a control.

TABLE 8

| Concentrations of Compositions (Weight %) | Absorptivity (%) after Aeration for | | | |
|---|---|---|---|---|
| | 0 | 1 | 2 | 7 |
| | | Days | | |
| 0.25 | 100 | 62.1 | 27.2 | 0 |
| 0.15 | 100 | 59.6 | 27.1 | 0 |
| 0.075 | 100 | 46.4 | 15.8 | 0 |
| 0.025 | 100 | 0 | 0 | 0 |
| 0.0125 | 100 | 0 | 0 | 0 |

However, the activated sludges were colored when the composition containing Nichilon Pure Blue 7G as a coloring agent was treated in the same manner as above, and the colored water was not decolored.

What is claimed is:

1. In a composition suitable for use in coloring toilet bowl flushing water which comprises a coloring agent in admixture with at least one member of the group consisting of a disinfectant, a perfume, a surfactant, a chelating agent, a pH adjusting agent, a filler and a binder the improvement according to which the coloring agent employed is at least one water soluble compound of the formula

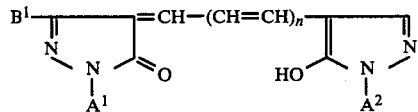

wherein
A$^1$ and A$^2$ are independently selected from the group consisting of (a) hydrogen, (b) lower alkyl of 1 to 4 carbons, (c) phenyl, (d) lower alkyl of 1 to 4 carbons having a water soluble radical selected from the group consisting of carboxylates and sulfonates of the formula —COOM and —SO$_3$M, respectively, and (e) phenyl or napthyl having at least one of the said water soluble radicals, wherein M is selected from the group consisting of an alkali metal, an alkaline earth metal, ammonium and lower alkylammonium wherein the alkyl has 1 to 4 carbons;

B$^1$ and B$^2$ are independently selected from the group consisting of (a) lower alkyl of 1 to 4 carbons, (b) phenyl, (c) carboxyl, (d) lower alkoxycarbonyl wherein the alkoxy has 1 to 4 carbons, and (e) phenyl or naphthyl having at least one of the said water soluble radicals, (f) hydroxyl, (g) lower alkoxyl of 1 to 4 carbons, (h) lower alkyl of 1 to 4 carbons having a carboxyl substituent, (i) lower alkyl of 1 to 4 carbons having a lower alkoxycarbonyl substituent wherein the alkoxyl has 1 to 4 carbons, (j) carbamoyl and (k) N-substituted carbamoyl wherein the substituent is lower alkyl of 1 to 4 carbons, phenyl or phenyl having a water soluble radical as defined above, and the numeral n is 0, 1 or 2.

2. A composition as claimed in claim 1 wherein
A$^1$ and A$^2$ are hydrogen;
B$^1$ and B$^2$ are methyl; and
the numeral n is 2.

3. A composition as claimed in claim 1 wherein
A$^1$ and A$^2$ are hydrogen;
B$^1$ and B$^2$ contain water soluble radicals of the formula —COOM in which M is selected from the group consisting of sodium, potassium and calcium; and
the numeral n is 2.

4. A composition as claimed in claim 1 wherein
A$^1$ and A$^2$ are selected from the group consisting of —(CH$_2$)$_p$COOM and —(CH$_2$)$_q$SO$_3$M in which the numeral p is 1 or 2, the numeral q is 1, 2, 3, or 4, and M is selected from the group consisting of sodium, potassium and calcium;
B$^1$ and B$^2$ are selected from the group consisting of lower alkyl of 1 to 4 carbons and phenyl; and
the numeral n is 2.

5. A composition as claimed in claim 4 wherein
A$^1$ and A$^2$ are methyl.

6. A composition as claimed in claim 1 wherein
A$^1$ and A$^2$ are lower alkyl of 1 to 4 carbons;
B$^1$ and B$^2$ are selected from the group consisting of lower alkoxycarbonyl in which the alkoxyl has 1 to 4 carbons, lower alkoxyl of 1 to 4 carbons, carbamoyl and N-substituted carbamoyl wherein the substituted is as defined above and
the numeral n is 2.

7. A composition as claimed in claim 1 wherein
A$^1$ and A$^2$ are phenyl;
B$^1$ and B$^2$ contain the water soluble radicals of the formula —COOM in which M is selected from the group consisting of sodium, potassium and calcium; and
the numeral n is 2.

8. A composition as claimed in claim 1 wherein
A$^1$ and A$^2$ are selected from the group consisting of phenyl and naphthyl both having at least one of the water soluble radicals of the formula —COOM and —SO$_3$M, respectively, in which M is selected from the group consisting of sodium, potassium and calcium;
B$^1$ and B$^2$ are selected from the group consisting of lower alkyl of 1 to 4 carbons, phenyl, carboxyl, lower alkoxy-carbonyl in which the alkoxy has 1 to 4 carbons, hydroxyl, lower alkoxy of 1 to 4 carbons, and N-substituted carbamoyl wherein the substituent is as defined above; and
the numeral n is 2.

9. A composition as claimed in claim 8 wherein $A^1$ and $A^2$ are selected from the group consisting of phenyl and naphthyl having at least one of the radicals, $-(CH_2)_p COOM$ and $-(CH_2)_q SO_3M$ in which the numeral p is 1 or 2, the numeral q is 1, 2, 3, or 4, and M is selected from the group consisting of sodium, potassium and calcium.

10. A composition as claimed in claim 1 in the form of an aqueous composition.

11. A composition as claimed in claim 1 in the form of a powdered composition.

12. A composition as claimed in claim 1 in the form of a molded composition.

13. A composition as claimed in claim 1 containing a binder of polyethylene glycol having a polymerization degree of about 6,000 to 20,000.

14. A composition as claimed in claim 12 wherein the composition is adapted to gradually dissolve in water.

15. A composition as claimed in claim 1 wherein the coloring agent is one which is decolored by chlorine type decoloring agents selected from the group consisting of chlorine gas and an aqueous hypochlorite solution.

16. A composition as claimed in claim 1 wherein the coloring agent is one which is decolored by decoloring treatment by bacteria in a treatment using activated sludges.

17. A composition as claimed in claim 11 wherein the composition is a mixture of the coloring agent and at least one powdered additive.

18. A composition as claimed in claim 12 wherein the composition is a solidified composition in a mold of melted polyethylene glycol having a polymerization degree of about 6,000 to 20,000.

19. In a method for coloring toilet bowl flushing water which comprises incorporating a coloring agent into the said water, the improvement according to which the coloring agent employed is at least one water soluble compound of the formula

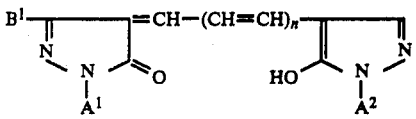

wherein
$A^1$ and $A^2$ are independently selected from the group consisting of (a) hydrogen, (b) lower alkyl of 1 to 4 carbons, (c) phenyl, (d) lower alkyl of 1 to 4 carbons having a water soluble radical selected from the group consisting of carboxylates and sulfonates of the formula $-COOM$ and $-SO_3M$, respectively, and (e) phenyl or naphthyl having at least one of the said water soluble radicals, wherein M is selected from the group consisting of an alkali metal, an alkaline earth metal, ammonium and lower alkylammonium wherein the alkyl has 1 to 4 carbons;

$B^1$ and $B^2$ are independently selected from the group consisting of (a) lower alkyl of 1 to 4 carbons, (b) phenyl, (c) carboxyl, (d) lower alkoxycarbonyl wherein the alkoxyl has 1 to 4 carbons, and (e) phenyl or npahthyl having at least one of the said water soluble radicals, (f) hydroxyl, (g) lower alkoxyl of 1 to 4 carbons, (h) lower alkyl of 1 to 4 carbons having a carboxyl substituent, (i) lower alkyl of 1 to 4 carbons having a lower alkoxycarbonyl substituent wherein the alkoxyl has 1 to 4 carbons, (j) carbamoyl and (k) N-substituted carbamoyl wherein the substituent is lower alkyl of 1 to 4 carbons, phenyl or phenyl having a water soluble radical as defined above, and
the numeral n is 0, 1 or 2.

* * * * *